(12) United States Patent
Ortiz et al.

(10) Patent No.: US 6,808,483 B1
(45) Date of Patent: Oct. 26, 2004

(54) IMPLANTABLE HEART ASSIST DEVICES AND METHODS

(75) Inventors: Mark Ortiz, Milford, OH (US); Paul A. Spence, 5818 Orion Rd., Louisville, KY (US) 40222

(73) Assignee: Paul A. Spence, Louisville, KY (US)

( * ) Notice: Subject to any disclaimer, the term of this patent is extended or adjusted under 35 U.S.C. 154(b) by 0 days.

(21) Appl. No.: 09/677,981

(22) Filed: Oct. 3, 2000

(51) Int. Cl.⁷ .............................................. A61N 1/362
(52) U.S. Cl. ......................................... 600/16; 600/37
(58) Field of Search .............................. 600/16–18, 37; 623/3.1

(56) References Cited

U.S. PATENT DOCUMENTS

| | | | |
|---|---|---|---|
| 2,826,193 A | 3/1958 | Vineberg ..................... 128/38 |
| 3,371,662 A | 3/1968 | Heid et al. ................. 128/24.5 |
| 3,496,932 A | 2/1970 | Prisk et al. .................... 128/64 |
| 3,587,567 A | 6/1971 | Schiff ....................... 128/24.5 |
| 4,048,990 A | 9/1977 | Goetz ........................... 128/64 |
| 4,192,293 A | 3/1980 | Asrican ........................... 128/1 |
| 4,304,225 A | 12/1981 | Freeman ....................... 128/60 |
| 4,506,658 A | 3/1985 | Casile ........................... 128/1 |
| 4,536,893 A | 8/1985 | Parravicini ...................... 623/3 |
| 4,583,523 A | 4/1986 | Kleinke et al. ................ 128/1 |
| 4,665,896 A | 5/1987 | LaForge et al. ................ 128/1 |
| 4,685,446 A | 8/1987 | Choy ............................ 128/1 |
| 4,925,443 A | 5/1990 | Heilman et al. .............. 600/16 |
| 4,979,955 A | 12/1990 | Smith ........................... 623/2 |
| 5,098,369 A | 3/1992 | Heilman et al. .............. 600/16 |
| 5,109,843 A | 5/1992 | Melvin et al. ............... 128/419 |
| 5,119,804 A | 6/1992 | Anstadt ........................ 128/64 |
| 5,131,905 A | 7/1992 | Grooters ....................... 600/16 |
| 5,139,517 A | 8/1992 | Corral ............................ 623/3 |
| 5,150,706 A | 9/1992 | Cox et al. .................... 128/400 |
| 5,169,378 A | 12/1992 | Figuera ........................ 600/16 |
| 5,176,619 A | 1/1993 | Segalowitz ................... 600/18 |
| 5,256,132 A | 10/1993 | Snyders ........................ 600/16 |
| 5,350,399 A | 9/1994 | Erlebacher et al. ......... 600/213 |
| 5,383,840 A | 1/1995 | Heilman et al. .............. 600/17 |
| 5,453,078 A | 9/1995 | Valentine et al. ............. 600/37 |
| 5,558,617 A | 9/1996 | Heilman et al. .............. 600/16 |
| 5,702,343 A | 12/1997 | Alferness ..................... 600/37 |
| 5,707,336 A | 1/1998 | Rubin .......................... 600/17 |
| 5,820,542 A | 10/1998 | Dobak, III et al. ........... 600/16 |
| 5,827,171 A | 10/1998 | Dobak, III et al. ........... 600/16 |
| 5,848,962 A | 12/1998 | Feindt et al. ................. 600/16 |
| 5,908,378 A | 6/1999 | Kovacs et al. ................ 600/16 |
| 5,957,977 A | 9/1999 | Melvin ......................... 623/3 |
| 5,961,440 A | 10/1999 | Schweich, Jr. et al. ....... 600/16 |
| 6,050,936 A | 4/2000 | Schweich, Jr. et al. ....... 600/37 |
| 6,059,715 A | 5/2000 | Schweich, Jr. et al. ....... 600/16 |
| 6,077,214 A | 6/2000 | Mortier et al. ................ 600/16 |
| 6,077,218 A | 6/2000 | Alferness ..................... 600/37 |
| 6,085,754 A | 7/2000 | Alferness et al. ........... 128/898 |
| 6,123,662 A | 9/2000 | Alferness et al. ............. 600/37 |
| 6,155,972 A | 12/2000 | Nauertz et al. ............... 600/37 |
| 6,162,168 A | 12/2000 | Schweich, Jr. et al. ....... 600/16 |
| 6,165,119 A | 12/2000 | Schweich, Jr. et al. ....... 600/16 |
| 6,165,120 A | 12/2000 | Schweich, Jr. et al. ....... 600/16 |
| 6,332,864 B1 | 12/2001 | Schweich, Jr. et al. ....... 600/16 |

FOREIGN PATENT DOCUMENTS

| | | |
|---|---|---|
| DE | 19933522 | 9/2000 |
| WO | WO 97/24101 | 7/1997 |
| WO | WO 98/29041 | 7/1998 |
| WO | WO 99/44534 | 9/1999 |
| WO | WO 00/06027 | 2/2000 |
| WO | WO 00/06028 | 2/2000 |

*Primary Examiner*—Scott M. Getzow
(74) *Attorney, Agent, or Firm*—Wood, Herron & Evans, L.L.P.

(57) ABSTRACT

Heart support and assist devices for supporting and assisting the pumping action of the heart. Various embodiments include mesh support devices, devices using straps, spiral-shaped devices, catheter-based devices and related methods.

12 Claims, 12 Drawing Sheets

IMPLANTABLE HEART ASSIST DEVICES AND METHODS

FIELD OF THE INVENTION

The present invention generally relates to devices used to physically support the heart and, alternatively, also actively assist the pumping action of the heart.

BACKGROUND OF THE INVENTION

The treatment of heart failure over the long term is a difficult problem. At the same time, weak cardiac muscle function is becoming an increasing problem. Patients are surviving longer and more patients are surviving myocardial infarcts leading to a large pool of patients who are inadequately served by current medical practice. Drug treatment to increase the strength of mycardial contraction has been unsuccessful over the long term. Recently, biventricular pacing (rather than the usual univentricular pacing) has been tried and this offers some promise in selected patients but is unlikely to solve the problem.

Devices will therefore remain the mainstay of treatment for terminal heart failure. Conventional methods have been unable to inject adequate energy into the cardiovascular system. Past attempts with the Jarvic heart or other replacement systems have met with problems such as failure due to thromboembolism. The patient is typically connected to a bulky internal or external controller and power supply for the heart replacement system. The inside of the artificial heart exposes a large artificial surface area to the flow of blood and clots develop as a result. These clots eventually break off and lodge in the brain leading to strokes or resulting in ischemic injury to other body organs. It has also been postulated that long-term exposure of blood to large artificial surfaces sets up a chronic inflammatory reaction which may predispose the patient to infection.

Currently, there are two major areas of development. A simplified system involves cannulation of the left ventricle or atrium with a tube-like structure and pumping of blood from this source into the aorta. A blood propeller system is located within the tubing of this system. A drive system powers the pump. The drive system can be located outside the patient, or can be implanted within the patient. If implanted, energy may be transmitted by induction coils from outside the body to the device. This device requires considerable residual cardiac function to operate. The heart must beat adequately to perform some function and usually only the left ventricle is supported by the device. Thus, right ventricular function must be adequate for survival.

The second and more complex pump is a totally implantable heart. The patient's heart is entirely removed or both ventricles are cannulated and artificial left and right ventricles are attached by a surgeon. The patient has a large surface exposed to the flow of blood as the blood comes in contact with the artificial ventricles, the connection tubes and the valves. Blood clotting, hemolysis and degradation of blood become problems in this situation.

For an entire generation, attempts have been made to create a heart assist device which leaves the native heart in place and squeezes the native heart. The blood is thus exposed only to the patient's natural tissue. Clotting on natural tissue is extremely rare. Pneumatically and electrically driven devices have been evaluated, but these devices have not reached clinical application. These devices have wrapped around the entire heart and squeezed both the left and right ventricles. Unfortunately, this does not mimic the way the heart contracts.

U.S. Pat. No. 4,925,443 illustrates a heart assist device including a tension band which is surgically placed within an interventricular muscle wall in order to compensate for weakness of the interventricular muscle wall or septum. An operating mechanism then opens and closes a pair of pressure plates to compress the left ventricle. The drawback to this device, however, is that the interventricular wall or septum experiences significant trauma due to the surgical implantation of the band within the wall or septum itself. Especially in cases in which the interventricular wall is already weakened, such trauma could severely damage the heart.

Another proposed device is disclosed in U.S. Pat. No. 5,119,804. With this device, the heart is placed within a cup having a vacuum source connected to hold the cup in position around the heart and having a pulsed pressure system to alternately apply relatively high positive and negative pressures to provide systolic and diastolic effects on the heart. This system, however, squeezes the entire heart muscle at one time and will tend to cause weaker portions of the heart to bulge outward while stronger portions of the heart muscle retain a normal shape. Therefore, the contraction applied to the heart muscle is not a natural one, but one that is dictated by the particular heart problems of the patient.

Another ventricular assist device is disclosed in U.S. Pat. No. 4,685,446. This device utilizes an inflatable balloon secured to the end of a catheter and inserted into the left ventricle. The balloon is inflated during left ventricular systole and then deflated in a repeating manner. Unfortunately, this device will also tend to cause weakened portions of the heart muscle to bulge around the left ventricle rather than causing the intended function of expelling blood from the ventricle. Thus, the ejection fraction of blood can be deficient with this device as well.

Despite the intuitively attractive nature of heart assist devices, no device has ever been clinically proven. Attention to some physiologic details will make the difference. The left ventricle is a thick-walled structure which propels blood into the systemic circulation at high pressure. The left ventricle is shaped as a truncated cone. During systole (contraction) this cone shortens along its length and narrows around its circumference. By this narrowing and shortening action, the internal volume of the left ventricular cavity decreases and blood is expelled. In a healthy heart, 60% to 70% of the blood volume (that is, the ejection fraction) is expelled on each beat. As the heart fails, the cavity enlarges, the heart wall thins and progressively smaller fractions of blood are expelled on each beat. In other words, the heart shortens and narrows much less during each beat.

The right ventricle has been described as a bellows pump. It wraps around and attaches to the circumference of the outside of the left ventricular wall. The outside wall of the right ventricle is considerably thinner than the wall of the left ventricle and also contracts against a lower pressure. The energy consumption of the right ventricle is therefore much lower than that of the left ventricle. The right ventricle expels blood when the muscle shortens and reduces the diameter of the crescent shaped cavity which is located between the outside wall the interventricular wall or septum shared with the left ventricle.

It is not surprising that merely squeezing the left and right ventricles with a device wrapped around both ventricles has not been successful. With previous devices, the left ventricle does not shorten from base to apex. There is also limited short axis shortening because the device does not squeeze the left ventricle in isolation, but with the right ventricle. To be effective the left ventricle requires more controlled compression. Generally, blood must be expelled from the ventricle in a more controlled and complete manner.

SUMMARY OF THE INVENTION

The present invention is generally directed toward heart support and assist devices including fully passive restraints, combinations of passive and active devices and fully active devices for assisting with heart contractions. Passive restraints generally include an external support member, which may be a strap, web or mesh, sheathing or other member configured to extend around the outside of the heart coupled with an internal support member extending within at least one of the ventricles and against one side of the interventricular septum. This type of passive restraining system can assist the heart muscle by supporting those portions of the muscle necessary to produce efficient contractions either naturally or with another active assist device. This support is provided in a manner that minimizes trauma to the heart muscle. Additional internal tensile members, such as cables, may be connected to the external tensile member or members longitudinally and/or transversely through one or both ventricles. These cables will assist with long axis and short axis shortening of the heart muscle during each contraction.

Combinations of passive and active devices may include, for example, external support members, in the form of straps, sheaths, wraps, mesh elements or webs, etc., combined with a blood pump connected for fluid communication directly with the left ventricle, right ventricle or both. Alternatively, a fluid inflatable bladder may be placed between the external tensile member and the outside surface of the heart to provide compression to one or both of the ventricles to assist in pumping blood through the heart. Finally, an active contraction device may integrate an external tensile member system with a powered actuator device to provide cyclical compression of the heart muscle through a pulling action on the tensile member or members.

In another aspect, the invention is directed to a heart assist device generally including a plurality of flexible tensile members adapted to be wrapped circumferentially about the heart of a patient. At least one tensile member is configured to extend around the left ventricle and a second tensile member is configured to extend around the right ventricle. A support member is configured to be received within the right ventricle against the interventricular septum and coupled to at least one of the first and second tensile members. This support member may be a portion of at least one of the tensile members or may be a separate member connected to at least one of the tensile members. At least one powered actuator may be operatively connected with the first and second tensile members and operates to pull the tensile members respectively against the left and right ventricles to expel blood therefrom.

More preferably, the heart assist device includes a plurality of tensile members configured to extend around the left ventricle and a plurality of tensile members configured to extend around the right ventricle. Each tensile member is secured at least indirectly to the support member. The support member is preferably a plate covered with a biocompatible material for inhibiting blood clotting. The actuator pulls the tensile members extending around the left ventricle against the outside surfaces of the heart and pulls the support member or plate against the interventricular septum in an opposing direction. The tensile members extending around the right ventricle are pulled against the left ventricle in an independent fashion.

One preferred embodiment of the invention may include a plurality of pulley members coupled with the tensile members and operating to allow a single powered actuator, such as an electric or pneumatic actuator, to pull multiple tensile members. Alternatively, multiple powered actuators may be used to independently pull the various tensile members. The tensile members, pulleys and other actuating structure may be contained in a suitable jacket or sheath positioned around the heart.

In accordance with another aspect of the invention, at least one internal tensile member is provided and configured to be connected lengthwise within the left ventricle between the mitral valve of the heart and the apex of the left ventricle. The internal tensile member inhibits lengthening of the ventricle when the powered actuator or actuators pull the tensile members to compress the left and right ventricles. As further options, transverse, internal tensile members may be connected within the left ventricle between the outside wall thereof and the interventricular septum to control widthwise expansion. Also, one or more internal tensile members may be utilized in the right ventricle for similar purposes.

As additional aspects of the invention, the tensile members may be contained in sleeves to prevent cutting of the heart by the tensile members during use. Also, a plurality of coronary obstruction preventing members may be used between the tensile members and the coronary arteries on the outside of the heart for preventing the coronary arteries from being compressed and obstructed by the tensile members.

The present invention also generally contemplates methods for assisting the pumping action of the heart. In a preferred embodiment, the method includes inserting an anchor member within the right ventricle and against the interventricular septum; encircling the outside of the right and left ventricles with respective tensile members; coupling the tensile members with the anchor member; and compressing the right and left ventricles by pulling the tensile members against the outside of the heart. Other methods will be apparent to those of ordinary skill based on a full review of this disclosure.

In various aspects of the invention, a basic device for assisting a heart may comprise a plurality of flexible, external tensile members adapted to be wrapped circumferentially around the heart of a patient. Preferably, this includes at least a first external tensile member configured to extend around the left ventricle and a second external tensile member configured to extend around the right ventricle. In accordance with the invention, an internal support member is configured to be received within at least one of the left and right ventricles and against the interventricular septum. This support member is coupled either directly or indirectly to at least one of the first and second external tensile members. The internal support member may comprise a portion of one or more of the external tensile members or may be a separate member, such as a plate, coupled with the external tensile members. The external tensile members are preferably flat straps or other similar structures that will not harm the outside of the patient's heart, and may be formed from any biocompatible material. In various embodiments, the support members may be implanted either partially or completely through one or more catheters.

In another embodiment of the invention, at least one of the first and second external tensile members may be configured generally in a spiral shape to facilitate the application of compression to the heart. In this embodiment, for example, one or more coils of the spiral may extend into one of the ventricles of the heart and bear against one side of the interventricular septum to form a support member as described above. An actuator is used to draw the spiral-shaped external tensile member into a tighter, coiled shape to actively compress or passively support one or both ventricles of the heart.

In another embodiment of the invention, the first and second external tensile members are configured as first and second halves of a cup. The cup is configured to envelop the patient's heart and comprises first and second shells with at least a first bladder configured for disposition between one of the shells and an outside surface of the heart. As with the other embodiments, one or more support members extend between opposite sides of the cup and within one or both ventricles of the heart to bear against the interventricular septum. A pump is provided for selectively inflating and deflating the bladder to apply compression to at least one of the left and right ventricles. In the preferred embodiment, a bladder is connected within each of the shells associated with the cup for compressing both of the ventricles. The support member or members are connected at a position generally between the first and second halves of the cup such as by being retained in place by the same connectors used to affix each half of the cup together. The cup may be formed in one, two or more pieces and, again, is formed from any suitable biocompatible material or materials as with all of the implantable components of each embodiment.

Various objectives, features and advantages of the invention will become more readily apparent to those of ordinary skill in the art upon review of the following detailed description taken in conjunction with the the accompanying drawings.

DETAILED DESCRIPTION OF THE PREFERRED EMBODIMENTS

Figure 1:
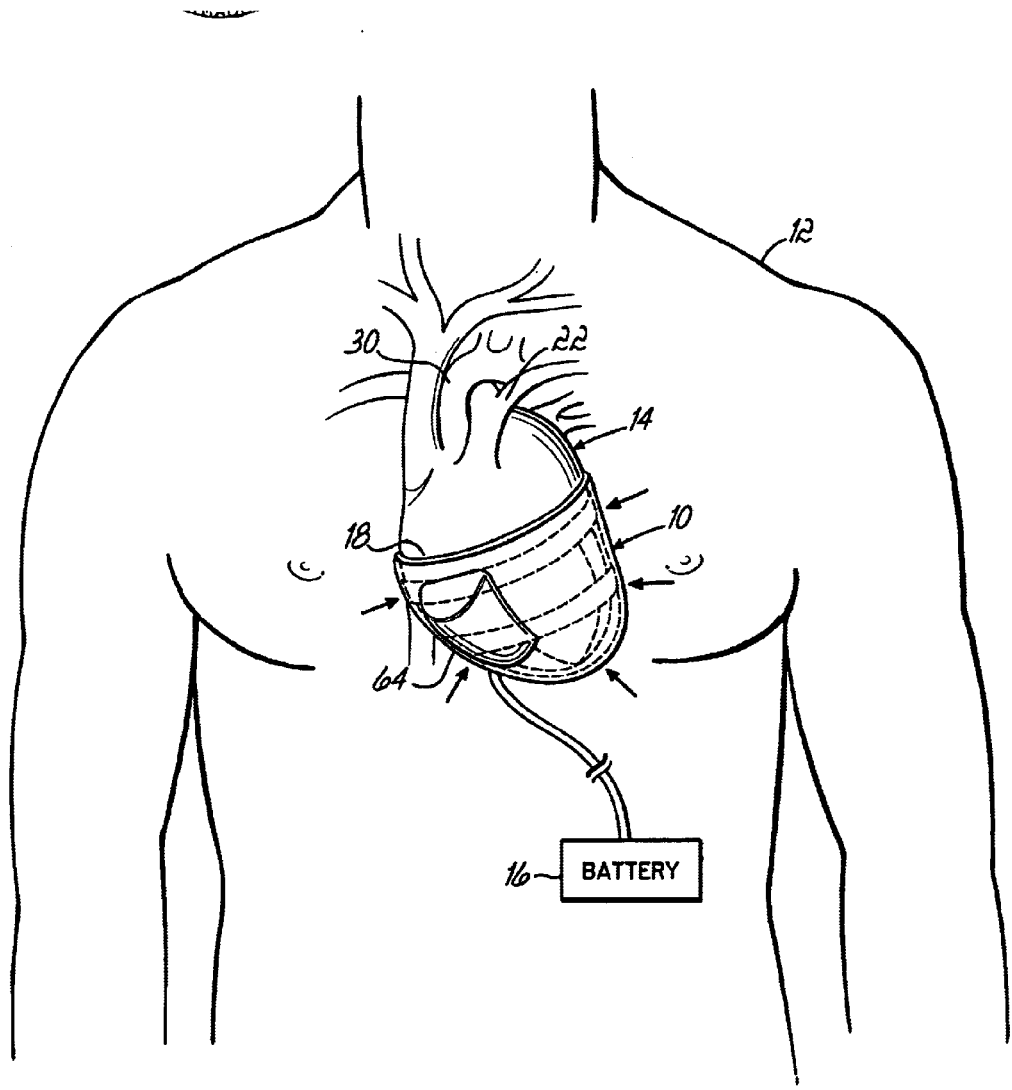
FIG. 1 is a perspective view showing one embodiment of the invention in an illustrative manner coupled to a patient's heart.
Figure 2:
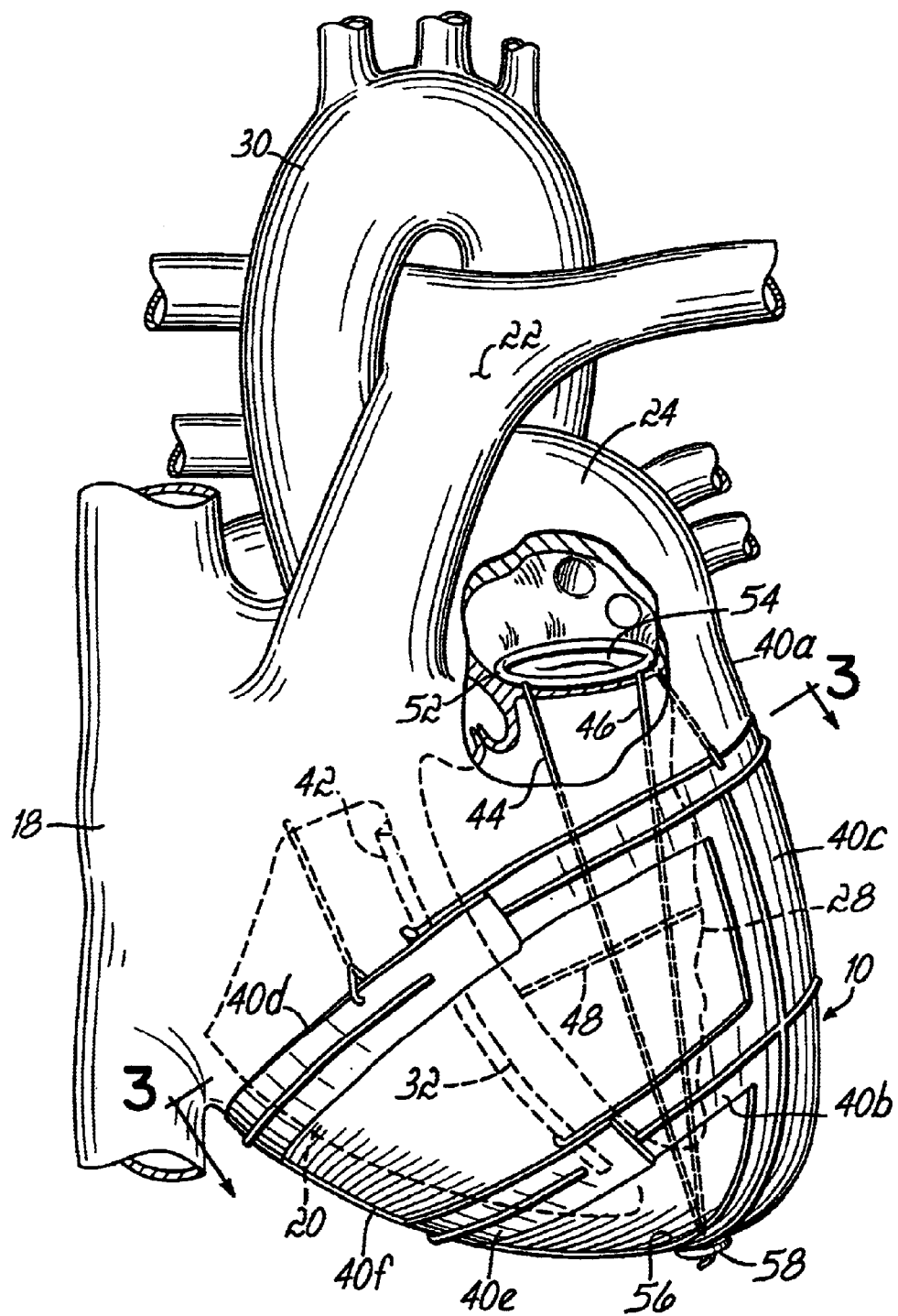
FIG. 2 is a partially fragmented perspective view showing the heart assist device of FIG. 1 coupled to the patient's heart.

FIG. 1 illustrates a heart assist device constructed in accordance with the invention and schematically illustrated implanted within a patient 12 in surrounding relation to the patient's heart 14. A power supply 16, such as an electric or pneumatic power supply, is operatively connected to heart assist device for reasons to be discussed below. As generally shown in FIG. 2, heart 14 has four chambers. The right atrium 18 receives blood flowing through veins in the patient's body. The right ventricle pumps the blood to the lungs of the patient through the pulmonary artery 22. The left atrium 24 receives oxygenated blood flowing back from the patient's lungs through the pulmonary vein and the left ventricle 28 pumps this blood out through the aorta to the patient's body. The right and left ventricles 20, 28 compress simultaneously during this pumping action and, in a normal heart, anywhere between about 50% and 80% of the blood in these chambers will be expelled as described above. In a heart weakened, for example, due to heart attack or other conditions, the efficiency of the heart will be reduced and, therefore, heart assist device will be used to increase the pumping action or expulsion of blood from the right and left ventricles 20, 28. An interventricular septum 32 separates the right and left ventricles 20, 28.

Figure 3:
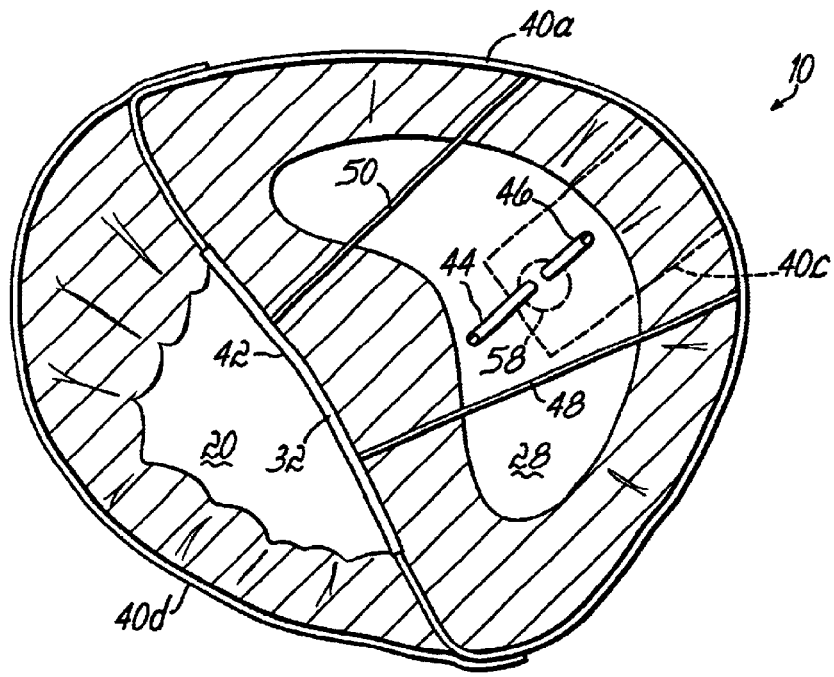
FIG. 3 is a cross sectional view taken generally along line 3—3 of FIG. 2.

As further shown in FIGS. 2 and 3, device preferably comprises a plurality of flexible tensile members 40a through 40f. In this embodiment, a flexible tensile member 40a is adapted to be wrapped circumferentially around left ventricle 28, as is another flexible tensile member 40b. A tensile member 40c may interconnect tensile members 40a and 40b as shown. A similar system is shown with tensile members 40d, 40e and 40f extending along the outside of right ventricle 20. Each of these tensile members is effectively connected to the other to form an integrated unit by connection to an internal support anchor member 42. In this embodiment, support member 42 comprises a plate surgically inserted into right ventricle and bearing against interventricular septum 32. Plate 42 may comprise a plate of rigid or semi-rigid polymeric material or metallic material covered in a biocompatible material adapted to resist blood clotting. Once plate 42 is implanted through a suitable incision into right ventricle 20, flexible tensile members 40a, 40b, 40d and 40e may be sutured thereto as shown in FIG. 2. Alternatively, one of the pairs of tensile members may be secured to plate 42, while the other pair is secured to the first pair.

As shown in FIG. 2, tensile members 40a through 40f may comprise flexible cables contained within a sheath or sleeve of biocompatible material. Internal flexible tensile members 44, 46, 48, 50 may be used to control the movements of the heart muscle as device is used to assist with the pumping action as described further below. Two tensile members 44, 46 may be secured between the annulus 52 of mitral valve 54 and the apex 56 of left ventricle 28. A button 58 may be used at the apex for securement purposes and may bear against the intersections of tensile members 40c, 40f. Transverse internal tensile members 48, 50 may extend crosswise as best shown in FIG. 3 between the outer wall of left ventricle 28 and the interventricular septum 32. Tensile members 48, 50 may be secured to any of the outer tensile members, as well as to plate 42 at opposite ends, or may be secured to the walls of the heart itself. Similar internal tensile members may be used in the right ventricle, although this is not preferred for the reason that it may not be necessary as the motion of the right ventricle is primarily in a direction toward the interventricular septum. Also, it will be understood that tensile members 44, 46 may be secured in other ways within left ventricle 28, such as by being secured to an annuloplasty ring or to a replacement mitral valve.

Figure 3A:
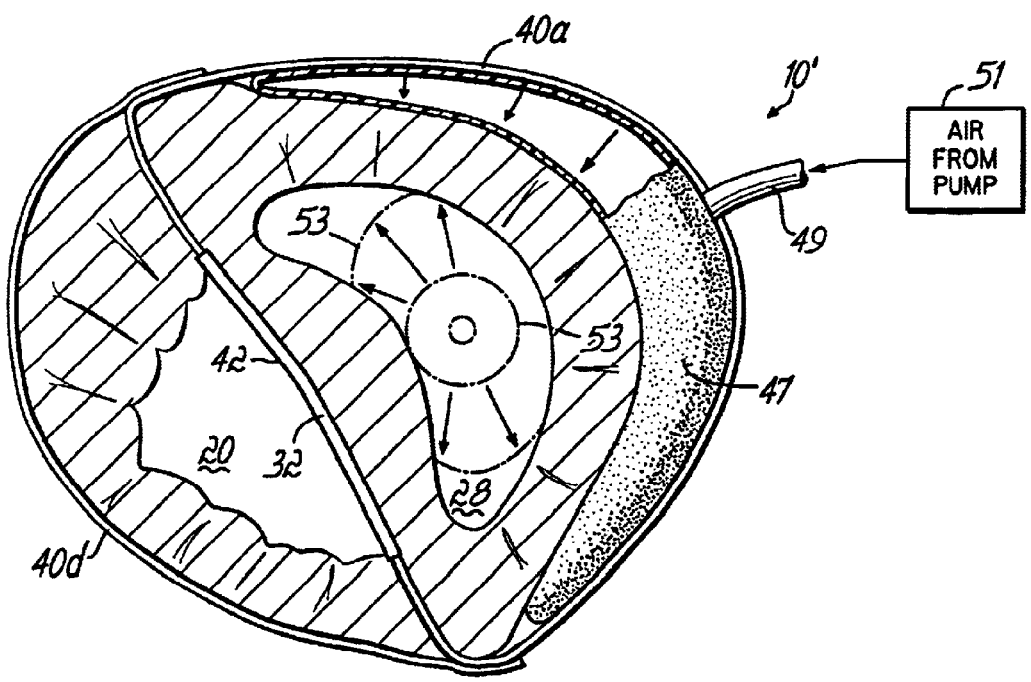
FIG. 3A is a cross sectional view similar to FIG. 3, but illustrating optional inflatable bladders for providing a pump assist to the heart.

FIG. 3A illustrates an alternative passive/active heart assist device 10' taking the form of a modified version of device shown in FIGS. 2 and 3. Device 10' includes various elements having like reference numerals in FIG. 3, but adds an inflatable bladder 47 which may be positioned between flexible tensile member 40a and the outside wall of left ventricle 28. Bladder 47 is connected through a suitable conduit 49 to a fluid pump which may direct air or other fluid into bladder 47 in a cyclical manner. Inflation and subsequent deflation of bladder 47 will contract left ventricle 28 against the support provided by internal support member 42 to expel blood and subsequent deflation will allow left ventricle 28 to expand and refill with blood. Alternatively, an internal bladder 53 may be provided and cyclically inflated and deflated, as shown, to expel blood from left ventricle 28 and allow subsequent refilling of the ventricle with blood. Bladder 53 would likewise be supplied with air or other appropriate fluid through a catheter from a suitable pump device (not shown).

Figure 4:
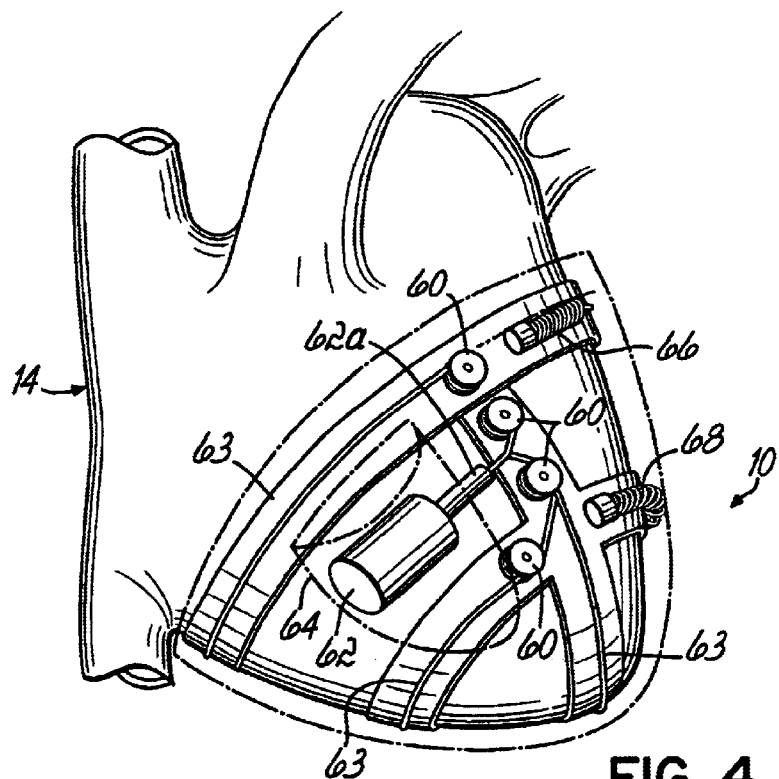
FIG. 4 is perspective view illustrating an embodiment with a single powered actuator for operating the heart assist device through the use of pulleys.

As further shown in FIG. 4, a series of pulley members 60 may be used with a single actuator 62, such as an electric solenoid or pneumatic actuator having a reciprocating element 62a attached to a series of cables or tensile members 63 extending through pulley members 60. Actuator 62 may be contained in a suitable pouch 64 or other containment structure and springs 66, 68 may be used to control the amount of compression applied by cables or tensile members 63. As reciprocating member 62 moves inwardly in the direction of the arrow in FIG. 4, cables or tensile members 63 will move under tension and cause simultaneous compression of the right and left ventricles.

Figure 5:
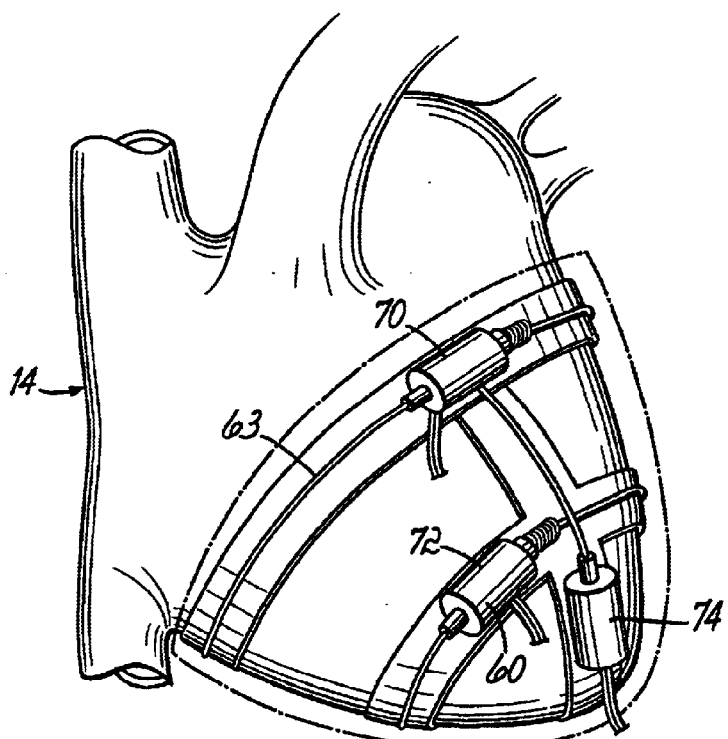
FIG. 5 is a perspective view similar to FIG. 4, but showing independent powered actuators.

FIG. 5 illustrates an embodiment similar to FIG. 4, but using multiple actuators 70, 72, 74 for independently applying compression to heart 14. Actuator 70 applies transverse compression to an upper portion of heart 14, while actuator 72 applies transverse compression to a lower portion of heart 14. Actuator 74 applies compression in a lengthwise direction. As with the other embodiments, suitable flexible tensile members, such as cables extending over or within straps, are provided to apply the compression upon operation of actuators 70, 72, 74.

Figure 6:
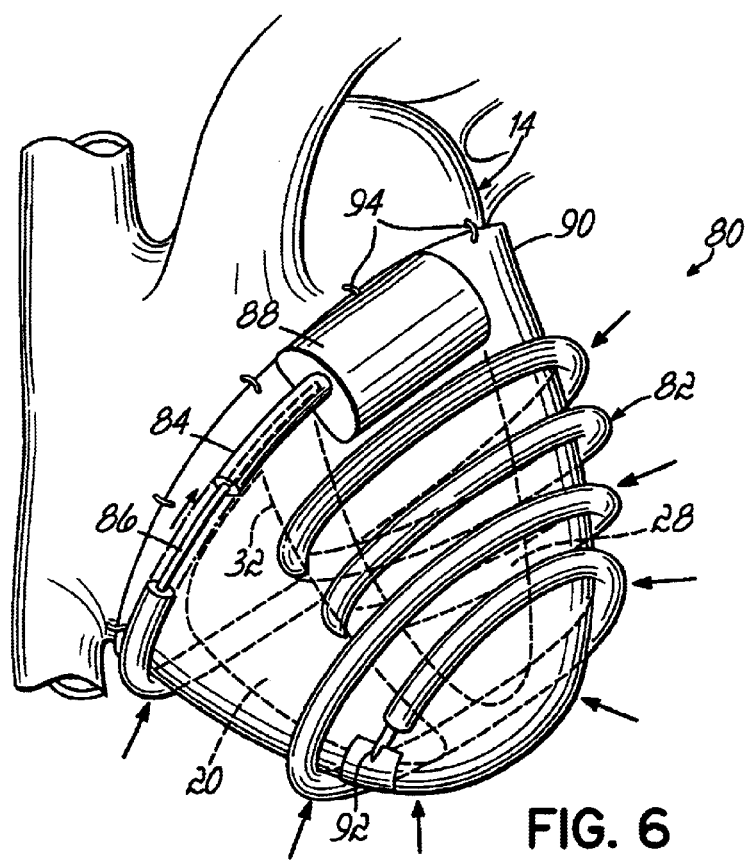
FIG. 6 is a perspective view of another alternative assist device comprising a spiral-shaped external tensile member.

FIG. 6 illustrates another alternative heart support and assist device 80 formed by a generally spiral shaped tensile member 82 extending around heart 14. Tensile member 82 preferably comprises an outer hollow member 84 and an inner movable cable 86 connected at one end to a suitable actuator 88 affixed to a jacket 90 and at an opposite end being rigidly affixed by a connector 92 to jacket 90. An upper end of jacket 90 may be suitably connected to heart 14, as through stitching 94. As shown in FIG. 6, two coils of the spiral tensile member 82 extend into right ventricle and bear against interventricular septum 32 before exiting heart 14 and again extending around the outside of jacket 90. The remaining upper and lower sets of coils extend around the outside of jacket 90. This configuration is intended to compress both the right and left ventricles 20, 28 of heart 14, while focusing on left ventricle 28, which is the ventricle with which most heart patients experience problems. Actuator 88 may be a conventional linear electric actuator that cyclically pulls on cable 86 in concert with the patient's own natural heart rhythm or as activated by a conventional pacing device which sets the patient's heart rhythm. It will also be appreciated that this type of generally spiral-shaped support device may be used in a passive manner without an active pump assist function. The spiral shape can be used for adjusting the tightness of tensile member 82 against the heart for achieving the proper amount of support.

Figure 7:
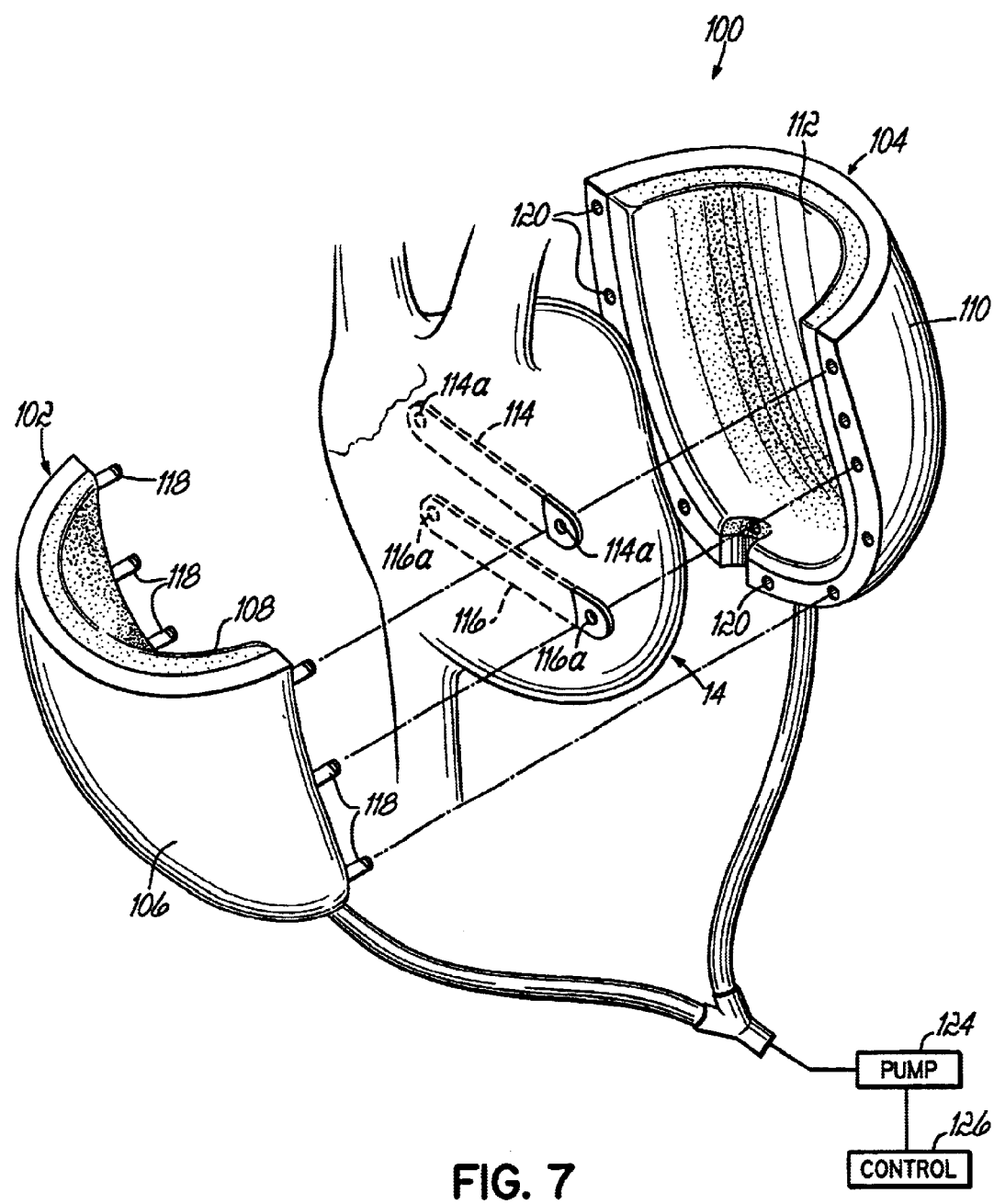
FIG. 7 is an exploded perspective view illustrating another alternative heart assist device comprised of a split cup and inflatable bladder system.

FIG. 7 illustrates another-alternative heart assist device 100 comprised of a cup having two halves 102, 104 which together receive a patient's heart 14. Each half 102, 104 is respectively comprised of an outer shell and innerinflatable bladder combination 106, 108 and 110, 112. One or more internal support members 114, 116 extend generally between halves 102, 104 through heart 14. Support members 114, 116 are intended to extend through one or both of the left and right ventricles (not shown) of heart 14 and bear against the interventricular septum (not shown), as with the support members used in other embodiments of the invention. This provides support for the interventricular septum during compression of the heart without a significant amount of trauma to the heart muscle. Support members 114, 116 may, for example, be one or more rigid plates or flexible straps, or other suitable support members. Respective connectors 118, 1may be provided to affix halves 102, 104 together. In this illustrative example, connectors 118 extend through holes 114a, 116a in support members 114, 116 and into connectors 120 of half 104 to connect device 100 firmly against heart 14. Additional connectors or other means may be used to ensure that device 100 remains in position around heart 14. Once in position, bladders 108, 112 may be cyclically inflated and deflated to compress the left and right ventricles of heart 14 while the opposite side of one or each of the ventricles is supported by members 114, 116. A pump 124 may be connected to bladders 108, 112 for selectively inflating and deflating bladders 108, 112 with an appropriate fluid, such as air or liquid. Again, pump 124 may be activated in correspondence with the patient's heart rhythm, such as through the use of a conventional electrical pacing device.

Figure 8:
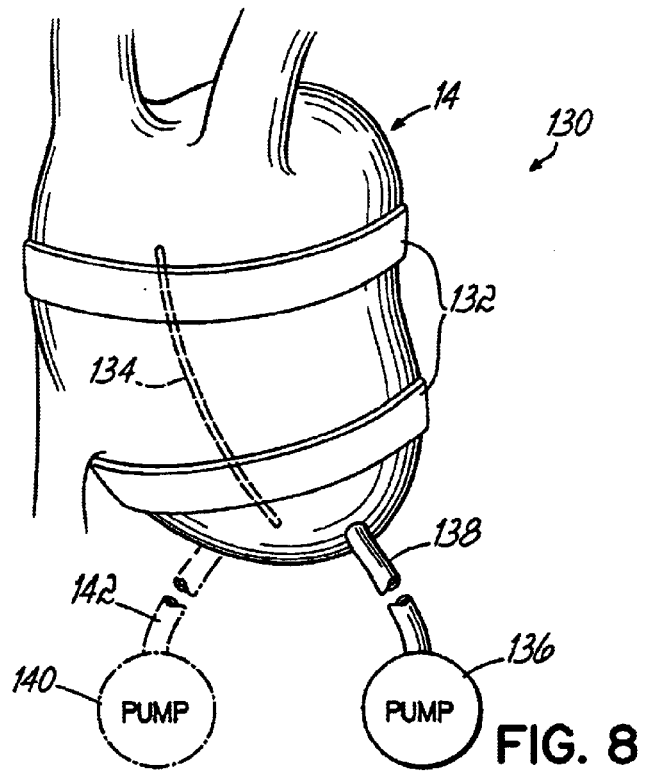
FIG. 8 is a perspective view of another alternative heart assist device used to directly pump blood into one or more heart chambers.

FIG. 8 illustrates another alternative heart assist device 130 comprised of a flexible strap system 132 configured for disposition around a patient's heart 14 and connected with a suitable internal support member 134 for bearing against one side of the interventricular septum within one of the heart's ventricles, as previously discussed. In this embodiment, at least one pump 136 is directly connected through a suitable conduit, such as a catheter 138, to one of the ventricles of heart 14. For example, pump 136 may be connected to the left ventricle of heart 14 for directly pumping blood into the left ventricle to assist with the movement of blood through heart 14. Likewise, another pump 140 may be directly connected to the right ventricle of heart 14 through another conduit 142 for assisting with blood flow through the right ventricle. Pumps 136 and 140 may obtain blood from any suitable vessel within the patient's body.

Figure 9:
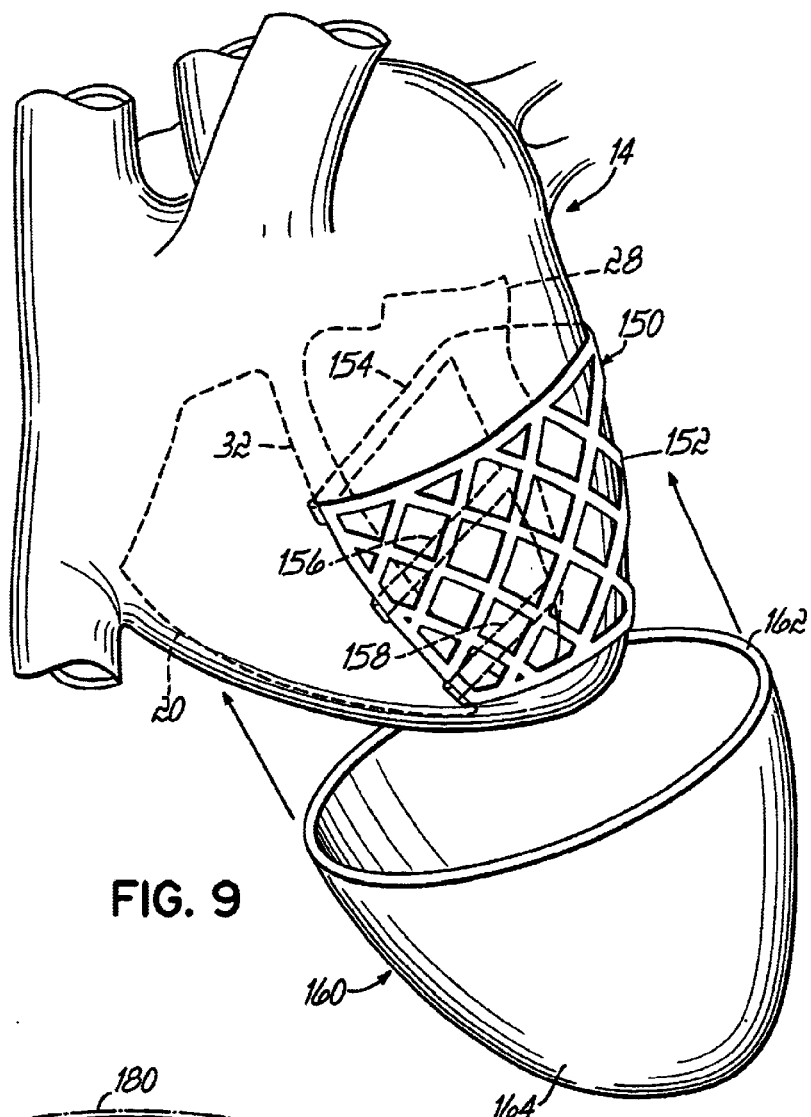
FIG. 9 is a fragmented perspective view of the heart with another embodiment of a passive heart support device implanted around the left ventricle.
Figure 11:
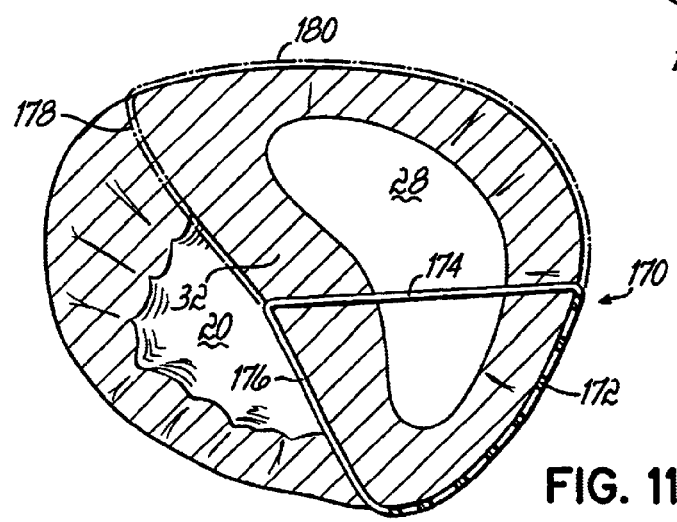
FIG. 11 is a transverse, cross sectional view of a heart with another alternative passive support device.

FIG. 9 illustrates a passive heart support device 150 shown implanted on a heart 14 and, specifically, around left ventricle 28. Support device 150 includes a flexible mesh or web material 152 serving as an external support member around left ventricle 28 and a plurality of internal support members 154, 156, 158 extending through right ventricle and against interventricular septum 32. Internal support members 154, 156, 158 may be attached to mesh or web element 152 in numerous ways, such as by stitching or other quicker connection means. At least one end of internal support members 154, 156, 158 will be detached from mesh or web element 152 for extension through right ventricle during implantation and then adjusted for tightness on heart 14 and secured to mesh or web element 152 preferably at an opposite side of the heart. If necessary, an external sheath 160, which may be elastic in nature, may receive heart 14 after attaching device 150, as a further securement means. Sheath 160 may include an open end 162 and a closed end 164.

Figure 10:
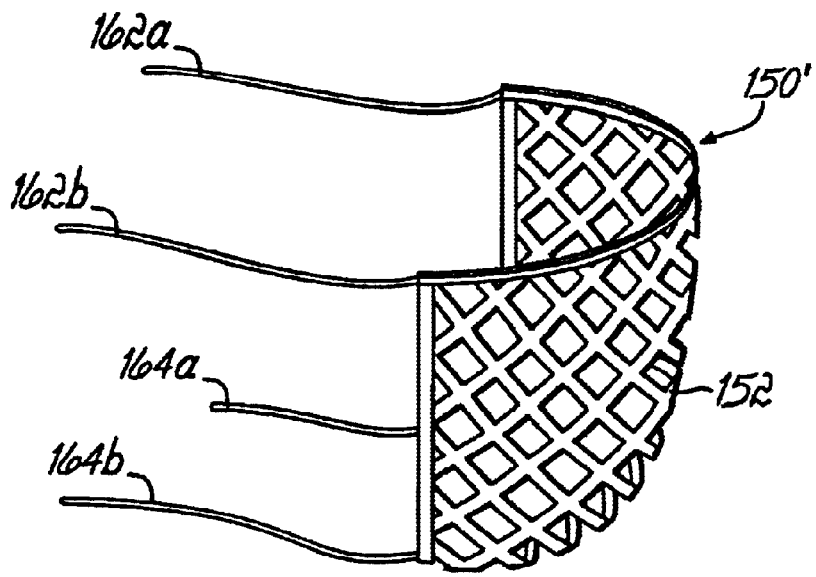
FIG. 10 is a perspective view of a passive heart support device similar to FIG. 9 but having alternative internal support members.

FIG. 10 illustrates an alternative device 150', which is similar to device 150, and includes a mesh or web element 152 for supporting an external portion of the heart. A plurality of internal support members 162a, 162b and 164a, 164b are connected to opposite sides of mesh element 152. Device 150', for example, may be introduced into a patient's chest through a relatively small port hole and, using catheter-based devices, internal support elements 162a, 162b and 164a, 164b may be secured across the interventricular septum as generally shown in FIG. 9.

FIG. 1 illustrates another alternative passive support device 170 comprising an external support portion 172, which may again be another flexible mesh or web element 172 and internal support member 174, 176. In this embodiment, support member 176 extends only partially along the interventricular septum 32 and internal support member 174 extends through septum 32 and connects with external support member 172 at one end and internal support member 176 at an opposite end. Support members 174 and 176 may be separate members which are connected together or may be a single integral member, as shown. Additional support members 178, 180, shown in phantom, may be optionally used in addition to or as an alternative to internal support member 174.

Figure 13A:
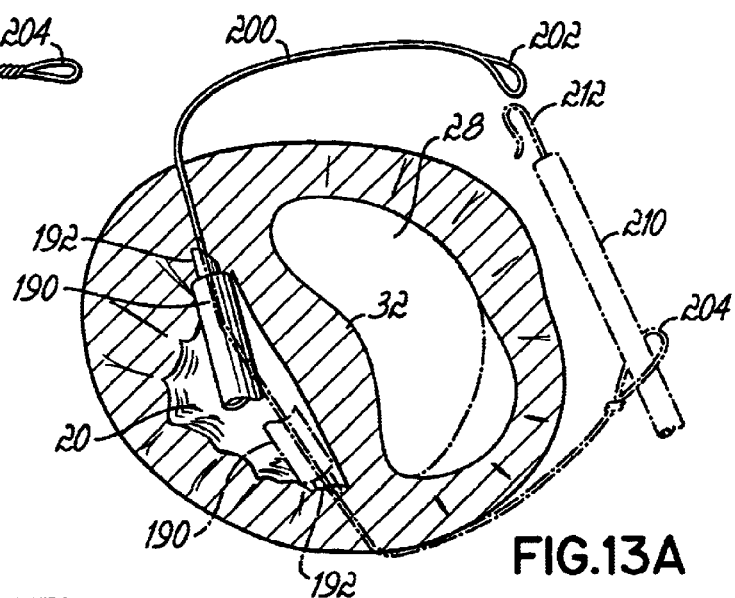
FIG. 13A is a schematic, cross sectional view of the heart during a later step of implanting the catheter-implanted support device.
Figure 13B:
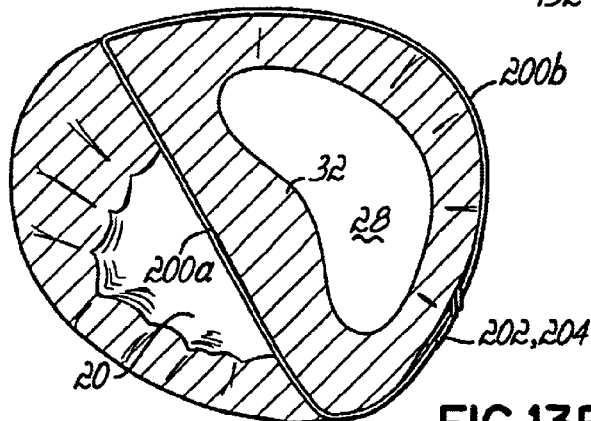
FIG. 13B is a cross sectional view similar to FIG. 13A, but illustrating the fully implanted, catheter-implanted passive support device.

FIGS. 12, 12A and 13A–B illustrate a partially catheter-based implantation device and method. Specifically, a catheter 190 having a sharpened portion 192 is introduced from a vein 194, for example, originating in the groin of the patient. Catheter 190 enters right atrium 18 and pierces through wall 18a into right ventricle 20. A heart support device 200 may comprise a cable which, for example, may include a sheath (not shown) and which acts as both an external and internal support members for heart 14. Catheter 190 may be used to introduce opposite ends of support device 200 through opposite walls of right ventricle 20, as shown in FIG. 13A. Piercing member 192 may, for example, extend to fully pierce through the wall of the heart, or device 200 itself may pierce through the wall of heart 14. Device 200 includes two looped ends 202, 204 with at least one of these ends being collapsible in the form of a tightening noose. In the embodiment shown, this is end 204. A tool 210 may be introduced through a small port hole in the patient's chest and includes a hook member 212. Tool 2extends through loop 204 and hook 212 may be used to grasp looped end 202 to pull it through looped end 204. Looped end 204 is then tightened as shown in FIG. 13B so that an internal portion 200a of device 200 lies against septum 32 within right ventricle and another portion 200b of device 200 lies on the external surface of heart 14 adjacent left ventricle 28.

Figure 14A:
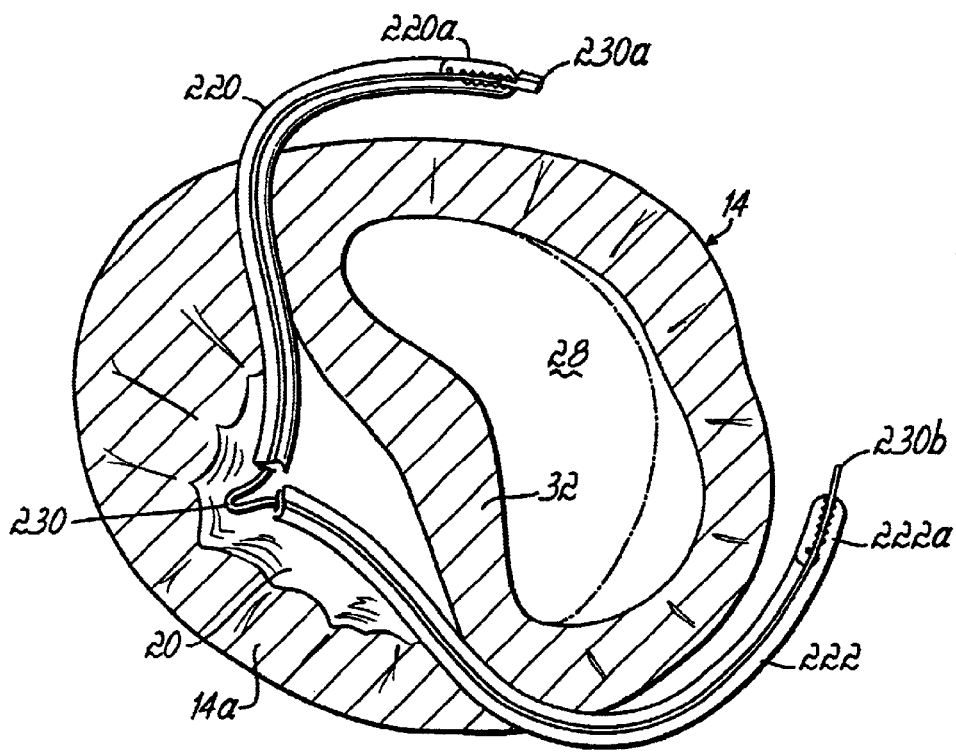
FIG. 14A is a transverse, cross sectional view of a heart schematically illustrating another catheter-based implantation method of a passive support device.
Figure 14B:
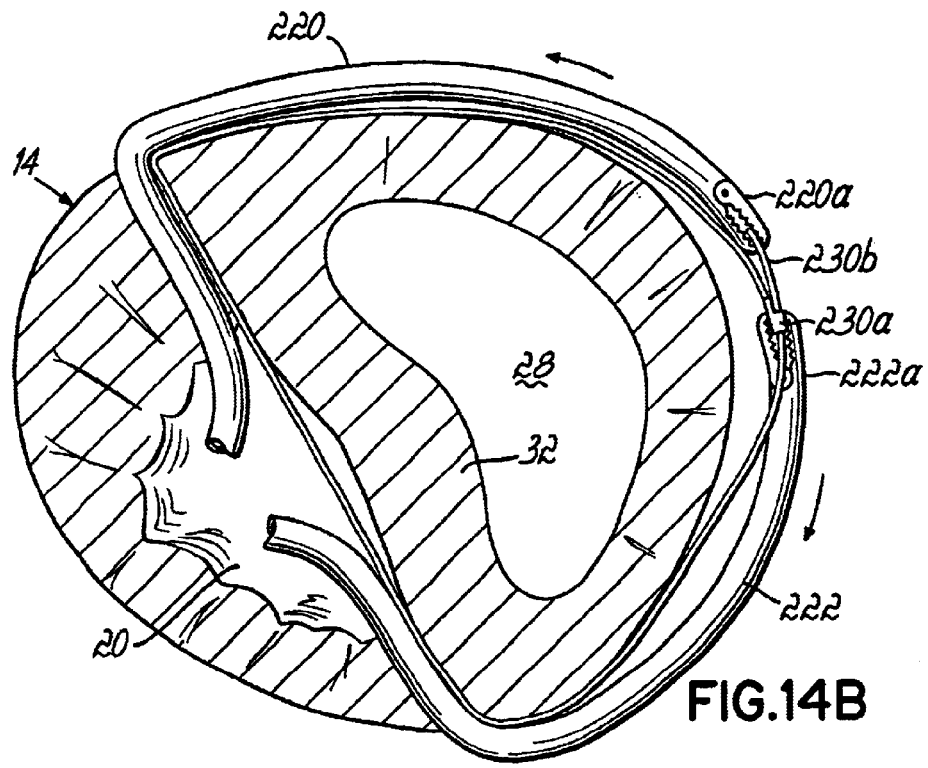
FIG. 14B is a cross sectional view similar to FIG. 14A, but illustrating a later point in the implantation procedure.
Figure 14C:
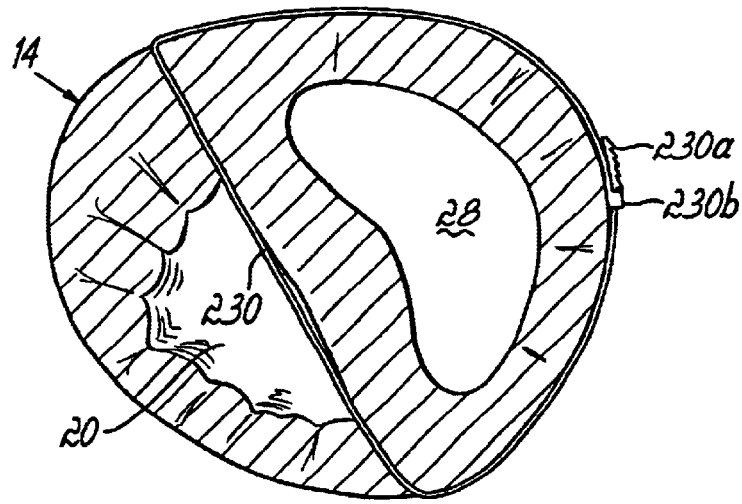
FIG. 14C is a cross sectional view similar to FIGS. 14A and 14B, but illustrating the fully implanted support device.

FIGS. 14A and 14B illustrate another alternative embodiment of the invention in the form of a completely catheter-based fixation method using first and second flexible gripper members 220, 222 which may be introduced through the same catheter (not shown) or separate catheters (not shown). Gripper members 220, 222 include jaws 220a, 222a which may be actuated to grip the ends of a support member 230. Support member 230 includes respective ends 230a, 230b retained between jaws 220a and 222a. As with the previous embodiment, gripper members 220, 222 may be introduced into right ventricle 20, pierced through the heart wall 14a adjacent septum 32 and directed around the outside of left ventricle 28. Support member 230 includes ratchet-type connector ends 230a, 230b which may be connected together as shown in FIG. 14B with end 230b being inserted into end 230a and retained by the teeth on end 230b. Jaws 220a, 222a release ends 230a, 230b and then are used to grip the opposite end 230a, 230b after engagement to allow pulling of the ends 230a, 230b in opposite directions for tightening and locking device 230 around left ventricle 28. It will be appreciated that other forms of the device, as well as other forms of the connecting and locking elements may be used as well. Also, other portions of the heart may be supported and this type of catheter-based insertion method and device may be used in conjunction with other supporting and/or assisting devices.

Figure 15:
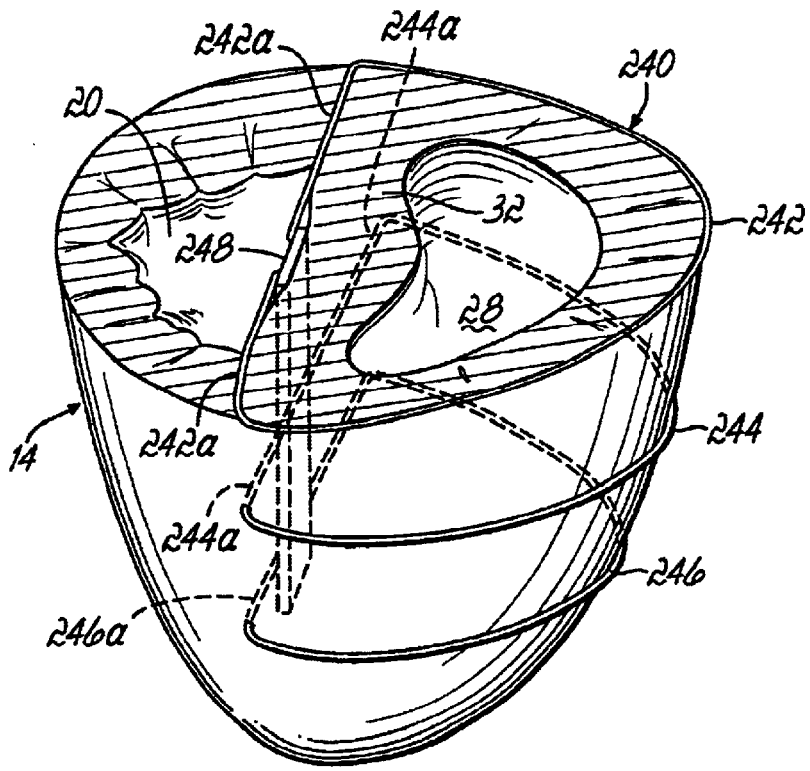
FIG. 15 is a partially sectioned, perspective view of a heart with another alternative passive support device affixed around the left ventricle.

FIG. 15 illustrates another alternative heart support device 240 comprised of three flexible support members 242, 244, 246 extending around the outside of left ventricle 28. Portions 242a, 244a and 246a extend through the wall of the heart into right ventricle and connect with a support plate 248 lying against septum 32.

Figure 17:
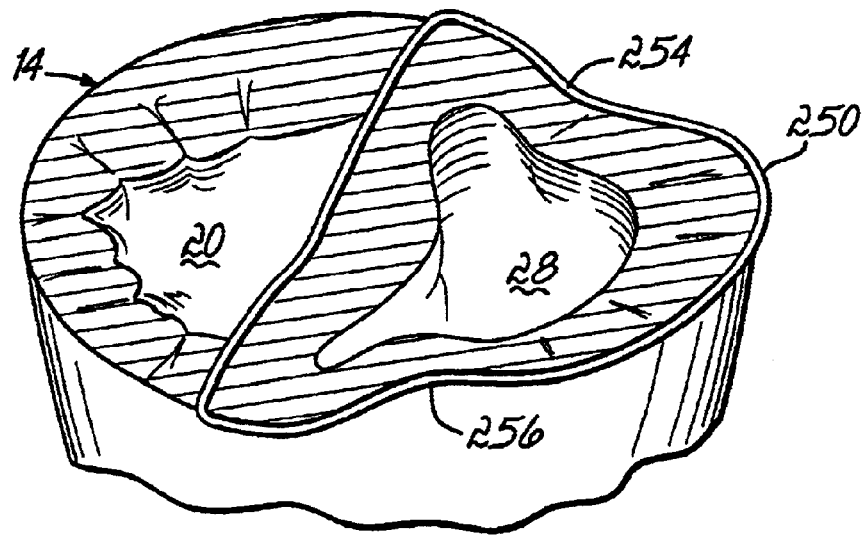
FIG. 17 is a schematic, cross sectional view of the heart shown in FIG. 16 with the device fully implanted around the left ventricle.
Figure 12:
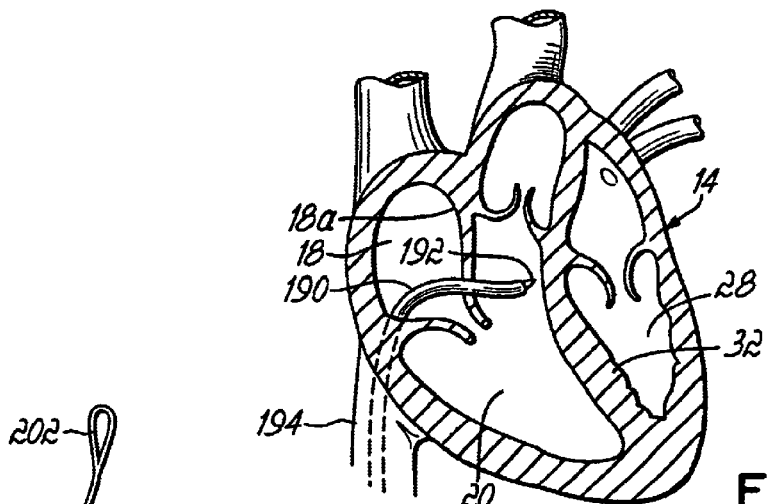
FIG. 12 is a cross sectional view showing an initial step of implanting a catheter-implanted heart support device.
Figure 12A:
FIG. 12A is a fragmented perspective view showing one embodiment of a catheter-implanted heart support device.
Figure 16:
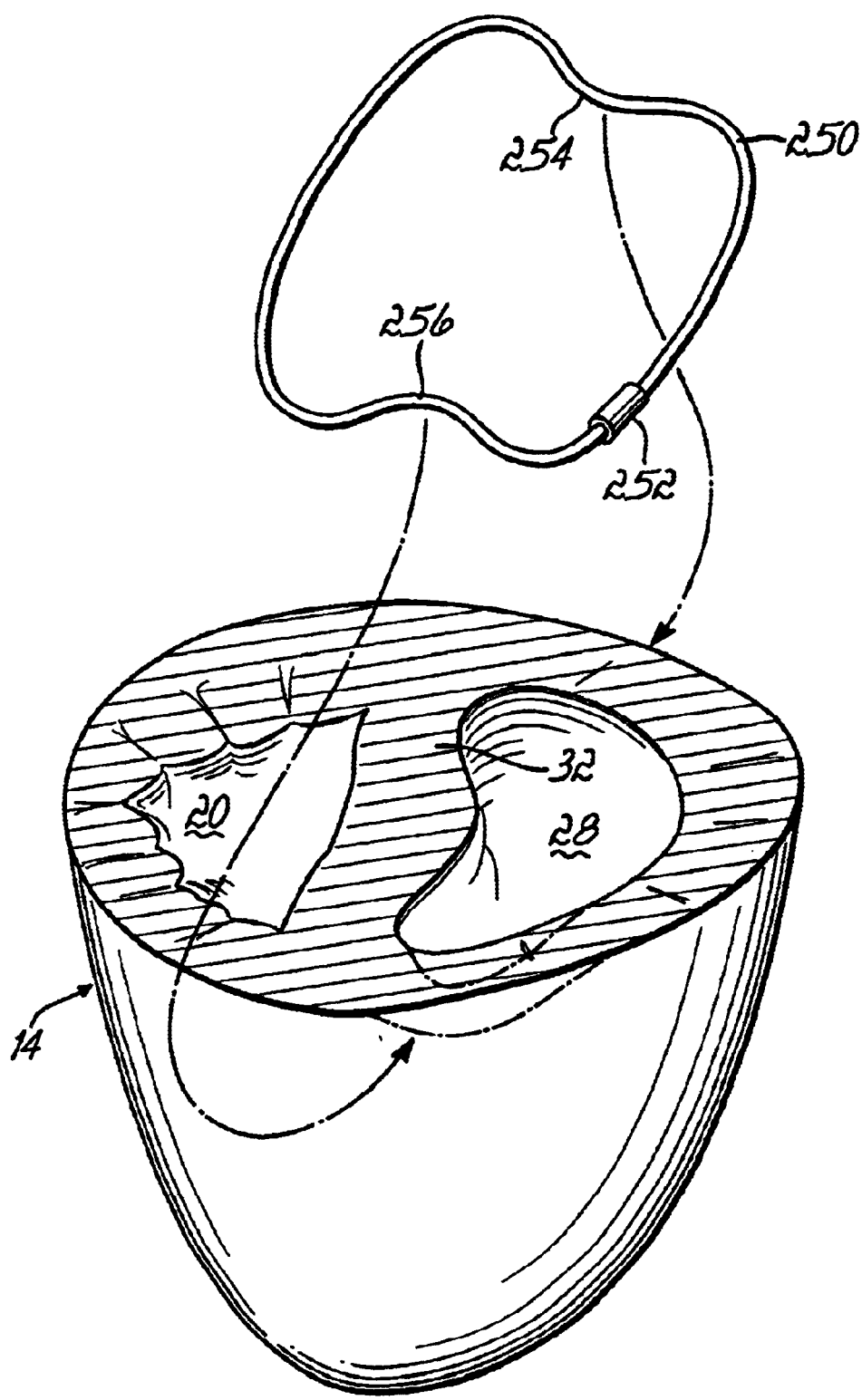
FIG. 16 is a schematic, perspective view showing the heart in cross section and another alternative passive support device.

FIGS. 16 and 17 illustrate another alternative passive heart support device 250 comprising a substantially rigid annular member having two ends (not shown) affixed to one another by a connector 252. Two inwardly projecting portions 254, 256 exert pressure selectively to small areas of the heart muscle. Specifically, for example, portions 254, 256 may be positioned to exert selective support to the papillary muscle regions of the heart, or to other weakened areas of the heart depending on the particular needs of the patient. Support member 250 is rigid enough to provide such support in a manner that prevents undesirable, outward bulging of the heart muscle. As apparent from FIG. 16, device 250 may also be configured to extend only around the outside surface of the heart.

While the present invention has been illustrated by a description of preferred embodiments and while these embodiments have been described in some detail, it is not the intention of the Applicants to restrict or in any way limit the scope of the appended claims to such detail. Additional advantages and modifications will readily appear to those skilled in the art. The various features and concepts of the invention may be used alone or in numerous combinations within each embodiment or between the embodiments depending on the needs and preferences of the user. This has been a description of the present invention, along with the preferred methods of practicing the present invention as currently known. However, the invention itself should only be defined by the appended claims, wherein

We claim:

1. A device for supporting a heart having left and right ventricles separated by an interventricular septum, the device comprising:

a first external, flexible element configured to be placed around at least a portion of the heart of a patient, and a flexible strap configured to be received within one of the left and right ventricles and against the interventricular septum, said flexible strap being-coupled to said first external, flexible element.

2. The device of claim 1, wherein said first external, flexible element further comprises a mesh comprised of intersecting fabric elements.

3. The device of claim 1, wherein said external, flexible element further comprises a mesh comprised of intersecting polymeric elements.

4. The device of claim 1, wherein said strap is adjustable to allow adjustable application of pressure to the heart.

5. The device of claim 1 further comprising multiple internal support members, each internal support member being formed as a flexible strap coupled to said first external, flexible element.

6. The device of claim 1, wherein said first external, flexible element is configured to overlie only a portion of one of said ventricles and said internal support member includes a first portion configured to lie against the interventricular septum in the other of said ventricles and a second portion configured to extend through said one ventricle and connect with said first external, flexible element.

7. A device for supporting a heart having left and right ventricles separated by an interventricular septum, the device comprising:

an external, flexible mesh element to be placed around at least a portion of the heart of a patient, a flexible strap configured to be received within one of the left and right ventricles and against the interventricular septum, said flexible strap being coupled to said external, flexible mesh element, wherein said external, flexible mesh element is configured to overlie only a portion of one of said ventricles and said flexible strap includes a first portion configured to lie against the interventricular septum in the other of said ventricles and a second portion configured to extend through said one ventricle and connect with said external, flexible mesh element.

8. A method of supporting a heart having left and right ventricles separated by an interventricular septum, the method comprising:

placing an external support element around an external surface of the heart adjacent at least one of the left and right ventricles, placing an internal support element within the other of the left and right ventricles and against the interventricular septum, adjusting the force of the external support element against the external surface of the heart by way of an adjustable connector on at least one of the internal and external support elements, and retaining the internal and external support elements on the heart at the adjusted force.

9. A device for supporting a heart having left and right ventricles separated by an interventricular septum, the device comprising:

a first external, flexible element configured to be placed around at least a portion of the heart of a patient, an internal support member configured to be received within one of the left and right ventricles and against the interventricular septum, said internal support member being coupled to said first external, flexible element, a second external, flexible element coupled to said first external, flexible element, wherein said first external, flexible element is configured to be placed around at least a portion of said left ventricle and said second external, flexible element is configured to be placed around at least a portion of said right ventricle, said first external, flexible element, second external, flexible element and said internal support member thereby giving independent support to said left and right ventricles, and at least one tensile member configured to extend through the left ventricle to provide additional support thereto.

10. The device of claim 9, wherein said first and second external, flexible elements further comprise strap members.

11. A device for supporting a heart having left and right ventricles separated by an interventricular septum, the device comprising:

a first external, flexible support element configured to be placed around at least a portion of the heart of a patient, and at least one tensile member connected to said first external flexible support element and configured to extend through the left ventricle to provide additional support thereto.

12. A method supporting a heart having left and right ventricles, the method comprising:

placing an external support element around an external surface of the heart, placing an internal tensile member within the left ventricle, and coupling the internal tensile member to the external support element in tension to provide support to the heart.

* * * * *

UNITED STATES PATENT AND TRADEMARK OFFICE
CERTIFICATE OF CORRECTION

| | |
|---|---|
| PATENT NO. | : 6,808,483 B1 |
| APPLICATION NO. | : 09/677981 |
| DATED | : October 26, 2004 |
| INVENTOR(S) | : Mark Oritz et al. |

It is certified that error appears in the above-identified patent and that said Letters Patent is hereby corrected as shown below:

Column 5

Line 45, change "34" to --3A--.

Column 6

Line 34, after "device" insert --10--.

Line 39, after "device" insert --10--.

Line 42, after "ventricle" insert --20--.

Line 46, after "aorta" insert --30--.

Line 53, after "device" insert --10--.

Line 57, after "device" insert --10--.

Column 7

Line 2, after "ventricle" insert --20--.

Line 16, after "device" insert --10--.

Line 38, after "device insert --10--.

Column 8

Line 18, after "ventricle" insert --20--.

Line 35, change "another-alternative" to --another alternative--.

Line 51, change "1may" to --120 may--.

Column 9

Line 20, after "ventricle" insert --20--.

Line 26, after "ventricle" insert --20--.

UNITED STATES PATENT AND TRADEMARK OFFICE
CERTIFICATE OF CORRECTION

PATENT NO. : 6,808,483 B1
APPLICATION NO. : 09/677981
DATED : October 26, 2004
INVENTOR(S) : Mark Oritz et al.

It is certified that error appears in the above-identified patent and that said Letters Patent is hereby corrected as shown below:

Column 9 (cont'd)

Line 44, change "1" to --11--

Column 10

Line 9, change "2extends" to --210 extends--.

Line 14, after "ventricle" insert --20--.

Line 46, after "ventricle" insert --20--.

Signed and Sealed this

Twenty-seventh Day of February, 2007

JON W. DUDAS
*Director of the United States Patent and Trademark Office*